(12) United States Patent
Shen et al.

(10) Patent No.: US 6,200,443 B1
(45) Date of Patent: Mar. 13, 2001

(54) GAS SENSOR WITH A DIAGNOSTIC DEVICE

(75) Inventors: Yousheng Shen, Salt Lake City; Franco Consadori, West Valley City, both of UT (US)

(73) Assignee: Atwood Industries, Inc., Rochester Hills, MI (US)

( * ) Notice: Subject to any disclaimer, the term of this patent is extended or adjusted under 35 U.S.C. 154(b) by 0 days.

(21) Appl. No.: 09/162,594

(22) Filed: Sep. 29, 1998

(51) Int. Cl.[7] .................................................. G01N 27/407
(52) U.S. Cl. ........................ 204/401; 204/421; 204/424; 204/426; 204/415
(58) Field of Search .................................. 204/421–429, 204/401

(56) References Cited

U.S. PATENT DOCUMENTS

| | | | |
|---|---|---|---|
| 3,400,054 | * 9/1968 | Ruka et al. ........................... | 204/426 |
| 3,928,161 | * 12/1975 | McIntyre et al. ..................... | 204/426 |
| 4,227,984 | 10/1980 | Dempsey et al. . | |
| 4,384,925 | * 5/1983 | Stetter et al. ........................ | 204/401 |
| 4,664,757 | 5/1987 | Zupancic et al. . | |
| 4,718,991 | 1/1988 | Yamazoe et al. . | |
| 4,820,386 | 4/1989 | LaConti et al. . | |
| 4,860,223 | 8/1989 | Grilk . | |
| 4,900,422 | * 2/1990 | Bryan et al. ......................... | 204/401 |
| 4,956,063 | * 9/1990 | Hale ..................................... | 204/401 |
| 5,133,857 | 7/1992 | Alberti et al. . | |
| 5,302,274 | 4/1994 | Tomantschger et al. . | |
| 5,331,310 | 7/1994 | Stetter et al. . | |
| 5,526,280 | 6/1996 | Consadori et al. . | |
| 5,573,648 | 11/1996 | Shen et al. . | |
| 5,650,054 | 7/1997 | Shen et al. . | |
| 5,691,704 | 11/1997 | Wong . | |
| 5,732,691 | 3/1998 | Maiello et al. . | |
| 5,764,150 | 6/1998 | Fleury et al. . | |
| 5,786,768 | 7/1998 | Chan et al. . | |
| 5,789,659 | 8/1998 | Williams . | |
| 5,798,700 | 8/1998 | Wong . | |
| 5,804,700 | * 9/1998 | Kwon et al. ......................... | 204/401 |
| 5,980,728 | * 11/1999 | Farber et al. ........................ | 204/401 |

* cited by examiner

Primary Examiner—T. Tung
(74) Attorney, Agent, or Firm—Banner & Witcoff, Ltd.

(57) ABSTRACT

A highly accurate, long life, low cost gas sensor is disclosed, particularly useful for measuring carbon monoxide and other toxic gases in an environment. The gas sensor has a first, sensing electrode and a second, counting electrode. Positioned between the first and second electrodes is an ion conducting, solid electrolyte membrane. In response to the presence of a toxic gas introduced to the first electrode, an electric signal is produced between the first electrode and the second electrode. The electric signal changes in response to changes in the concentration of the toxic gas. Detection circuitry measures the electric signal to determine the concentration of the toxic gas. An electrically conductive, hydrophobic top membrane electrically connects the first electrode to the detection circuitry while preventing liquid water from contacting the first electrode. An electrically conductive, hydrophobic bottom membrane electrically connects the second electrode to the detection circuitry. The top and bottom membranes, though hydrophobic, are preferably also microporous so as to be gas permeable, including permeable to water vapor. Preferably the top and bottom membranes are ion insulating as well. Optionally the sensor is provided with a water reservoir to maintain constant relative humidity at the ion conducting electrolyte membrane. The sensor may also have a heating element. Internal and external self-diagnostic features to ensure that the sensor is functioning normally are disclosed, as well as self-calibration features, so as to ensure sensor accuracy.

14 Claims, 11 Drawing Sheets

REACTION AT SIDE I:
$$CO + H_2O \rightarrow CO_2 + 2H^+ + 2e^-$$

REACTION AT SIDE II:
$$2H^+ + 2e^- + 1/2 O_2 \rightarrow H_2O$$

REACTION AT SIDE I:
$$H_2 \longrightarrow 2H^+ + 2e^-$$

REACTION AT SIDE II:
$$1/2 O_2 + 2H^+ + 2e^- \longrightarrow H_2O$$

REACTION AT SIDE I:
$O_3 + 2e^- + 2H^+ \rightarrow O_2 + H_2O$

REACTION AT SIDE II:
$H_2O \rightarrow 1/2 O_2 + 2H^+ + 2e^-$

REGULAR CO MEASUREMENT

INTERNAL SELF-DIAGNOSTIC

EXTERNAL SELF-DIAGNOSTIC

GAS SENSOR WITH A DIAGNOSTIC DEVICE

FIELD OF THE INVENTION

The present invention generally relates to gas sensors, and more particular to improved gas sensors for detecting carbon monoxide and other toxic gases.

BACKGROUND OF THE INVENTION

Gas sensors for sensing carbon monoxide (CO) and other toxic gases are used in a wide variety of applications, from commercial and residential markets to automobiles and recreational vehicles to scientific instrumentation. Several technologies are currently known for measuring carbon monoxide.

One type of toxic gas sensor is sometimes referred to as a semiconductor gas sensor. Typically such sensors use a ceramic semiconductor, such as tin oxide, in combination with a catalyst such as palladium or platinum for catalytic combustion of the toxic gas. Commercial examples include Figaro Model No. TGS-822 available from Figaro, Inc. (Japan). In the presence of a catalyst and heat, a toxic gas such as carbon monoxide undergoes a catalyzed reaction at the surface of the semiconductor, changing the conductivity of the sensor. Conductivity of the sensor rises as the concentration of toxic gas rises, and this change can be measured by detection circuitry.

Such semiconductor based sensors have several problems and limitations. Semiconductor based sensors operate only at high temperatures, typically in the range of 200° C. to 500° C. and therefore require a heating source to create a detectable electrical signal. Further, sensors of this type are sensitive to changes in humidity. Also, other oxidizable or reducible gases will readily react with the sensor in the normal, high temperature operating condition, increasing the chances of generating a false positive signal. Moreover, semiconductor based toxic gas sensors have inherent limitations in their sensitivity and accuracy and are expensive to manufacture.

Another type of toxic gas sensor is a gel type sensor, also referred to as a biomimetic type toxic gas sensor. In this type of sensor organo-metallic materials are used in a gel with a catalyst. Exposure to carbon monoxide changes the color of the gel. An optical scanner detects the change in the color of the gel. Such sensors, however, are slow to respond to changes in carbon monoxide concentration, never completely recover their original color after exposure to carbon monoxide and, to a greater degree than the semiconductor based sensors, have inherent limitations in accuracy.

Another type of toxic gas sensor is an electrochemical sensor, based upon use of a liquid acid electrolyte. Carbon monoxide is exposed to a cathode. A liquid acid electrolyte connected to the electrode acts as a protonic conductor, carrying protons between a cathode and an anode. An electric signal generated by the reaction is proportional to the concentration of carbon monoxide sensed at the cathode. Unfortunately, carbon monoxide sensors in accordance with this type of technology suffer from accuracy problems due at least in part to corrosion by the acid, by the liquid drying over time, and the inherent limitations in the signal generated by the liquid acid. Furthermore, the acidity of such sensors changes with time. Change in the acidity of these kinds of liquid electrolytes causes these kinds of sensors to quickly lose accuracy. In addition to these problems, to measure the concentration level of the toxic gas which is desired to be detected, an electric potential (typically provided by a DC power source) must be applied across the sensor. Constant application of a DC power source acts to polarize the sensor, so that the electric signal generated drifts over time with the changes in this polarization voltage.

Recently, more robust, low cost and accurate electrochemical toxic gas sensors have been developed, based on the use of solid protonic conductive polymer membranes. Examples of protonic conductive membrane based toxic gas sensors include U.S. Pat. No. 5,573,648 to Shen et al and U.S. Pat. No. 5,650,054 to Shen et al. When the sensor is exposed to a toxic gas such as carbon monoxide, an electric signal is generated. The greater the carbon monoxide level, the greater the electric signal. More specifically, carbon monoxide reacts with moisture in the air at room temperature at a sensing electrode to produce carbon dioxide, protons and electrons in a reaction as follows.

$$CO+H_2O \rightarrow CO_2+2H^++2e^-$$

The protons (hydrogen ions) migrate across a protonic conductive electrolyte membrane to a counting electrode where they react with oxygen in a reaction as follows.

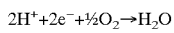

$$2H^++2e^-+\tfrac{1}{2}O_2 \rightarrow H_2O$$

Sensors of this type are advantageous in that, in addition to substantially improved accuracy, they can function with no need for an external power source to force the reaction. This reduces costs of the sensor and reduces power consumption, a feature which is advantageous for battery operated devices.

It is desirable to have the electrodes formed thin to minimize internal electronic resistance. In the '054 patent to Shen et al, one of the electrodes 14 has a portion which necessarily extends down into contact with a current collecting bottom washer around a nonconductive membrane in order to complete the electrical connection through the sensor. This is inconsistent with the objective of making the electrodes as thin as possible.

It would be highly desirable to provide an improved toxic gas sensor which would have an enhanced electric signal generated in the presence of toxic gas, especially carbon monoxide, to facilitate improved measurement, accuracy and reduced response time by a toxic gas detector employing such a sensor. It would also be highly desirable to provide an electrochemical toxic gas sensor which protects its electrodes from exposure to liquid water. Further, it would be highly desirable to provide an improved toxic gas sensor which is operable under a wide range of temperatures. It would also be highly desirable to provide an electrochemical and toxic gas sensor which has self-diagnostic features, and to provide a toxic gas sensor having self-calibration features.

In view of the foregoing, it is an object of the present invention to provide a gas sensor for sensing carbon monoxide and other toxic gases having an electrical signal generated in response to sensing a toxic gas and to provide protection for its electrodes from exposure to liquid water. It is an additional object of the present invention to provide a carbon monoxide and toxic gas sensor for use in a gas detector having fast response times. It is an additional object of the present invention to provide a gas sensor which operates properly even under very low temperatures. It is still another object of preferred embodiments of the present invention to provide an electrochemical toxic gas sensor having a self-diagnostic feature to indicate when the sensor is not functioning normally, and/or a sensor having a self-calibration feature to indicate when the sensor is accurately measuring the amount of toxic gas present in the sensed environment. It is an additional object of preferred embodiments of the present invention to provide a carbon monoxide and toxic gas sensor that is of low cost, compact size, easy to manufacture and which is highly reliable in operation.

SUMMARY OF THE INVENTION

There is provided a low cost sensor for sensing gas, especially carbon monoxide and other toxic gases, which has a first, sensing electrode exposed to the gas to be sensed and a second, electrode. Positioned between the first electrode and the second electrode is an ion conducting solid electrolyte membrane. When a toxic gas such as carbon monoxide is introduced from an external environment to the first, sensing electrode, an oxidation reaction takes place at the first electrode, and protons and electrons are liberated. The protons migrate across the ion conducting membrane to the second electrode where they react with oxygen and electrons to form water. An electric signal is thus generated between the electrodes in response to the presence of the toxic gas, and the electric signal is proportional to the concentration of the toxic gas. This electric signal can be measured by detector circuitry to determine the concentration of the gas.

To avoid having the first electrode directly exposed to the sensing environment an electrically conductive top membrane is positioned between the sensing environment and the first electrode. Gas from the environment diffuses across the electrically conductive membrane to increase the locations where the reactions can occur. In addition, the electrically conductive membrane is hydrophobic, that is, liquid water cannot pass through it to reach the sensing electrode and disturb the reaction rate.

The ion conducting membrane typically is humidity sensitive. A water vapor source can be provided to provide nearly constant hydration to the ion conducting electrolyte membrane. Typically such a water vapor source may comprise a water reservoir positioned behind the second electrode on the side opposite the sensing electrode, but care must be taken to prevent water from the reservoir from contacting the second electrode, as the presence of liquid water will affect the rate of the reaction and consequently the electric signal generated by the sensor. Furthermore, protons (hydrogen ions) exist in water under ambient conditions, and if liquid water reaches the electrodes, the protons will migrate across the protonic conductive membrane and disrupt accurate measurement. The present sensor has an electrically conductive, hydrophobic bottom membrane positioned proximate to the second electrode to protect the second electrode from exposure to liquid water. However, while hydrophobic, the bottom membrane is also microporous so that water vapor from the water reservoir can pass through the bottom membrane to reach the electrodes and ion conducting membrane to maintain nearly constant hydration. The top and bottom membranes are ion insulating, meaning that protons which disassociate in liquid water are prevented from migrating to the ion conducting membrane.

The measured levels of CO or other toxic gases are dependent upon the internal resistance of the sensor. This internal resistance is affected if the electrodes are flooded with water. Preferably, top and bottom electrically conductive, hydrophobic membranes sandwich the electrodes and the ion conducting membrane between them. In addition to the protection provided the electrodes from flooding, these top and bottom membranes give the sensor increased sensitivity and greater accuracy. The top membrane is electrically conductive, completing the electrical connection between the top electrode and the detector circuitry for the electric signal.

Current collecting top and bottom washers serve to sandwich the top membrane and bottom membrane. The washers are electrically conductive and are positioned in a housing which is crimped or otherwise loaded under pressure to ensure appropriate electrical connection. The housing can also hold the above discussed reservoir of water.

In accordance with another aspect, a heating element may be provided to keep the solid electrolyte membrane warm even when the temperature drops below the freezing point of the liquid in the reservoir. A resistance element may be positioned proximate to the solid electrolyte membrane. A dc power source can pass current through the resistive element, generating heat sufficient to warm the solid electrolyte membrane so that water stays in the liquid phase. Preferably the resistance element is not in electrical communication with the rest of the sensor.

In accordance with another aspect, a self-diagnostic feature can be incorporated into the detector circuitry. A power source can apply a voltage across the sensor and the rate of change of electric signal received from the sensor once the power source is removed can indicate whether the sensor is functioning properly. A microprocessor or other suitable electric measuring device can control the magnitude and duration of the power source pulse, and can measure the rate of change of the electric signal and compare it with known value ranges for a healthy sensor. Self-diagnostic features of this kind can measure, for example, the capacitance of the sensor or, alternatively, the sensor can act as a fuel cell where the power source generates an electrochemical reaction at one of the electrodes, producing a volatile gas. If the sensor is healthy, once the power is removed, the sensor consumes the volatile gas, generating an electrical signal which is measured and compared by the microprocessor.

In accordance with another aspect, an externally mounted self-diagnostic feature can be provided. The first electrode is exposed to a reactive gas, released by the self diagnostic feature, producing an electrochemical reaction and generating a corresponding electric signal. External self-diagnostic sensors of the present invention have an advantage in that they can determine whether a sensor sampling hole is plugged. The amount of the reactive chemical released can be controlled by, for example, a microprocessor which would also receive the electric signal generated by the sensor in response to introduction of the reactive chemical, compare it with a known or predetermined value range for a healthy sensor, and create an output which could be sent to a display.

In accordance with another aspect, a self-calibration feature can be incorporated with the sensor, wherein the first electrode is exposed to a measured or otherwise controlled release of a reactive chemical from a source external to the toxic gas sensor. An electrochemical reaction occurs, generating an electric signal. This received electric signal can be compared with a known value corresponding to the concentration of the reactive chemical expected at the first electrode as a result of such measured release. An output signal can be produced which compensates for any difference between the received electric signal and the known value. Compensation could take the form, for example, of a bias voltage or a recalibration of sensor parameters.

From the foregoing disclosure and the following more detailed description of various preferred embodiments it will be apparent to those skilled in the art that the present invention provides a significant advance in the technology and art of gas sensors for sensing carbon monoxide and other toxic gases. Particularly significant in this regard is the potential the invention affords for providing a carbon monoxide sensor of low cost, reliability, durability and long life. Additional features and advantages of various preferred embodiments will be better understood in view of the detailed description provided below.

Figure 1:
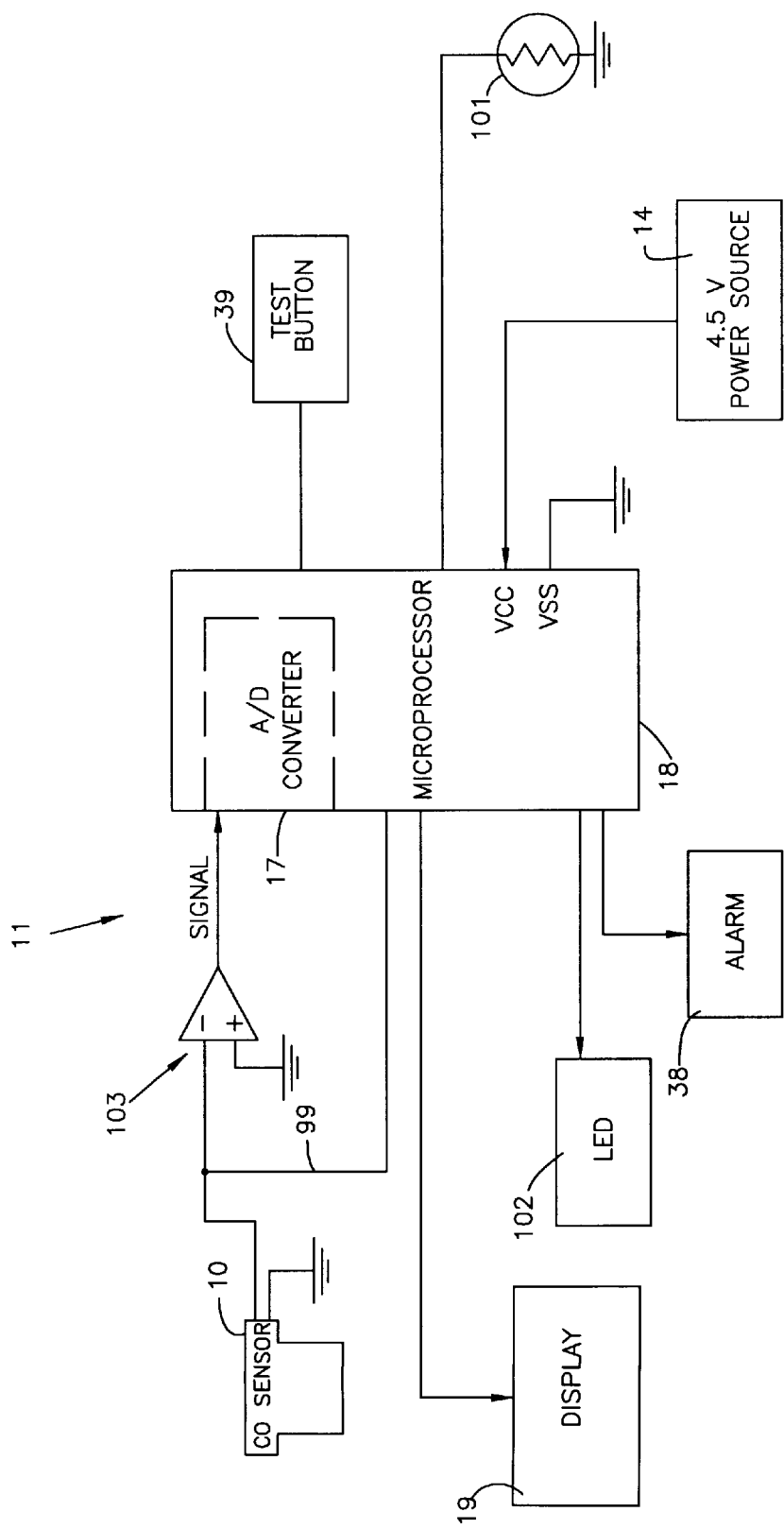
FIG. 1 is a diagram of the detector circuitry used to measure the electrical signal generated by a toxic gas sensor in accordance with the present invention when a toxic gas such as CO is introduced to the sensor at the first electrode.

It should be understood that the appended drawings are not necessarily to scale, presenting a somewhat simplified representation of various preferred features illustrative of the basic principles of the invention. The specific design features of the toxic gas sensors disclosed here, including, for example, the cross sectional thickness of the solid electrolyte membrane, and the specific composition of the electrically conductive, hydrophobic membranes will be determined in part by the particular intended application and use environment. Certain features of the illustrated embodiments have been enlarged or distorted relative to others to facilitate visualization and clear understanding. In particular, thin features (such as the electrodes) may be thickened for clarity of illustration. All references to direction and position, unless otherwise indicated, refer to the orientation of the toxic gas sensor illustrated in the drawings. In general, lateral or laterally refers to a rightward or leftward direction in the plane of the paper in FIG. 1, and top and bottom refers to corresponding directions in the plane of the paper in FIG. 1. The same reference numerals are used in the drawings to identify identical features of different preferred embodiments. It will be readily understood that toxic gas sensors in accordance with the present invention can be aligned in a variety of positions without affecting their performance.

DETAILED DESCRIPTION OF CERTAIN PREFERRED EMBODIMENTS

It will be apparent to those skilled in the art, that is, to those who have knowledge or experience in this area of technology, that many design variations are possible for the gas sensors disclosed herein. The following detailed discussion of various alternative and preferred features and embodiments will illustrate the general principles of the invention with reference to a gas sensor suitable for measuring carbon monoxide and used in a carbon monoxide detector for use in residential or commercial buildings and recreational vehicles. Other embodiments suitable for other applications including scientific applications and automotive applications will be apparent given the benefit of this disclosure.

Referring now to the drawings, FIG. 1 shows a diagram for a toxic gas sensor 10 and detector circuitry 11 in accordance with a preferred embodiment. Detector circuitry 11 may include a programmed processor such as microprocessor 18 to regulate and control the detector circuitry and other functions of the sensor 10. An electric signal is received from the sensor by microprocessor 18, or other suitable electric signal measuring device, optionally after passing through an analog to digital (A/D) converter 17, converting the analog electric signal generated by the sensor 10 into a digital value. The electric signal is proportional to the sensed concentration level of carbon monoxide. Once the input electrical signal, typically a voltage, is measured by the microprocessor 18, an output signal is directed to a display, for example, LED display 102 and/or LCD display 19, which can show the concentration of the gas, typically in parts per million (ppm). As another option for formatting the output signal for a display, if the signal from the sensor is above a given critical threshold, thereby indicating that toxic gas concentrations are unacceptably high, then the microprocessor can also direct an output signal to an alarm 38, which can be a light, buzzer or beeper. Unacceptably high levels can be expressed for example, as an absolute value such as 100 parts per million carbon monoxide. Alternatively the unacceptably high level can be determined with reference to a specification such as Underwriters' Laboratories Carbon Monoxide Standard 2034.

A power source 14 can be, for example, three 1.5 Volts AA batteries connected in series, and connected to the rest of the detector circuitry 11 through a diode (not shown) to prevent damage from reverse installation of the batteries in a manner well know to those skilled in the art. Test button 39 can be pushed by an operator to engage a self-diagnostic feature, sending a diagnostic pulse along lead 99 across to the sensor 10. Self-diagnostic features are described in greater detail below.

Figure 11:
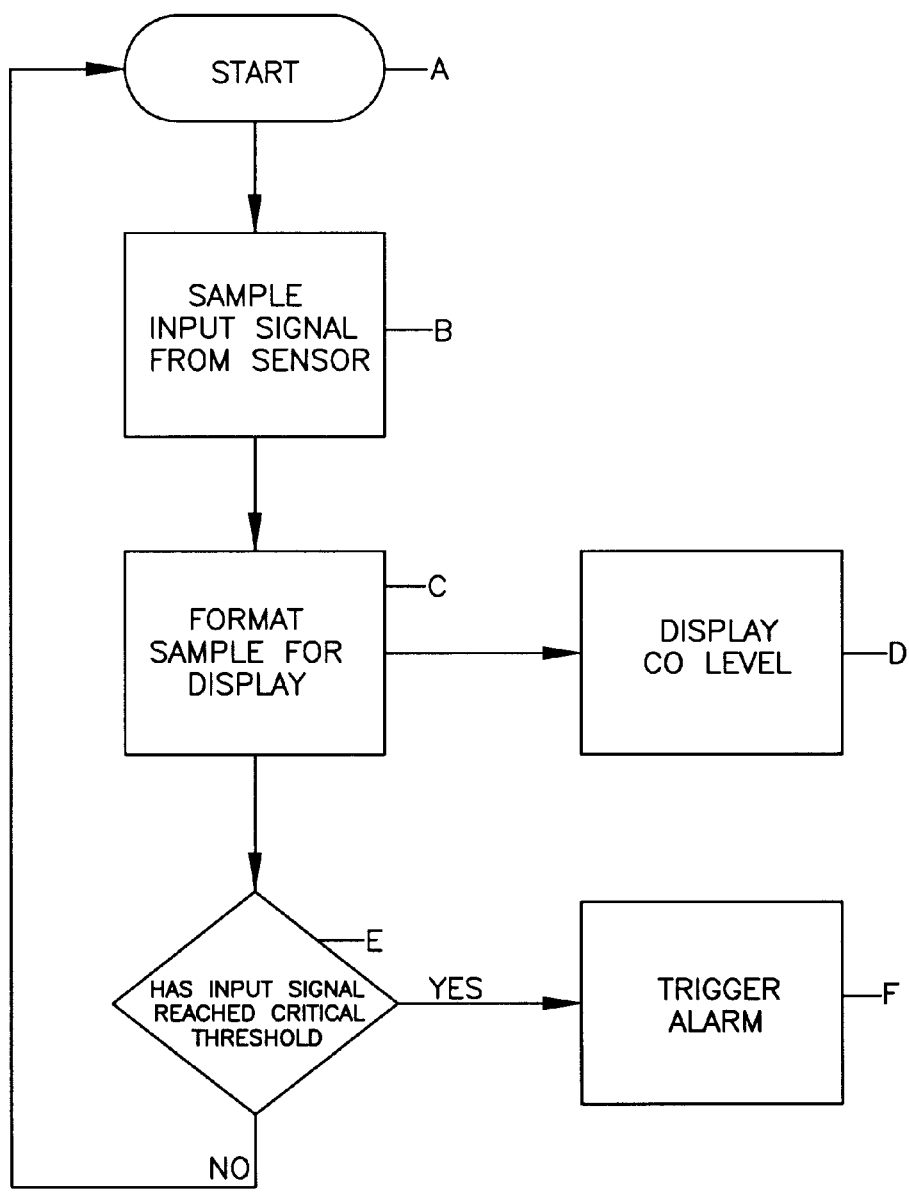
FIG. 11 shows a flow chart for a preferred operation of regular measurement and display of the concentration of the toxic gas present in the environment at the sensor.

FIG. 11 shows one embodiment of a logic block diagram for the toxic gas sensor. From Start A, the input signal from the sensor is measured at B by a microprocessor. The microprocessor generates an output signal at C, which is formatted for display, and this output is sent to display 19 at D. A decision block E checks to see if the CO level is above a level which is considered unsafe, e.g., 100 ppm. Alternatively, instead of checking a single instantaneous level Block E can represent an averaging of multiple values, sampled at block B to determine a concentration over time. If the threshold level has been reached, an alarm 38 is triggered at F.

Modifications may be made to the sensor's electric signal before it reaches the microprocessor, including for example, positioning a low input impedance amplifier 103 to receive the electric signal from the sensor. Other signal conditioning devices, such as high input impedance amplifiers, integrators and oscillators may be also used. For example, as all microprocessors have a clock, (usually a crystal clock, not separately shown) timing intervals can be determined with great precision. Thus, another way of measuring the electric signal generated by the sensor 10 in response to CO is to measure voltage-with-time changes or current-with-time. Examples of suitable microprocessors for use in the present invention include model 16c622 or others in the 16c series of 8-Bit CMOS microcontrollers from MICROCHIP TECHNOLOGY. Other suitable microprocessors will be readily apparent to those skilled in the art giver the benefit of this disclosure. Other measurement devices, including voltage meters for measuring potential difference across the sensor and ammeters for measuring current generated by the sensor will be readily apparent to those skilled in the art given the benefit of this disclosure.

The toxic gas to be measured can be, for example, a gas which is oxidizable at room temperature in the presence of a catalyst, especially carbon monoxide. Other reactive gases may be detectable and can form the basis for diagnostic features mounted externally of the sensor, as described in greater detail below. Advantageously, many gases which will react in the high heat needed in a semiconductor based sensor are unreactive at room temperature in electrochemical sensors in accordance with the present invention, thereby reducing the occurrence of false positive signals for carbon monoxide.

Figure 2:
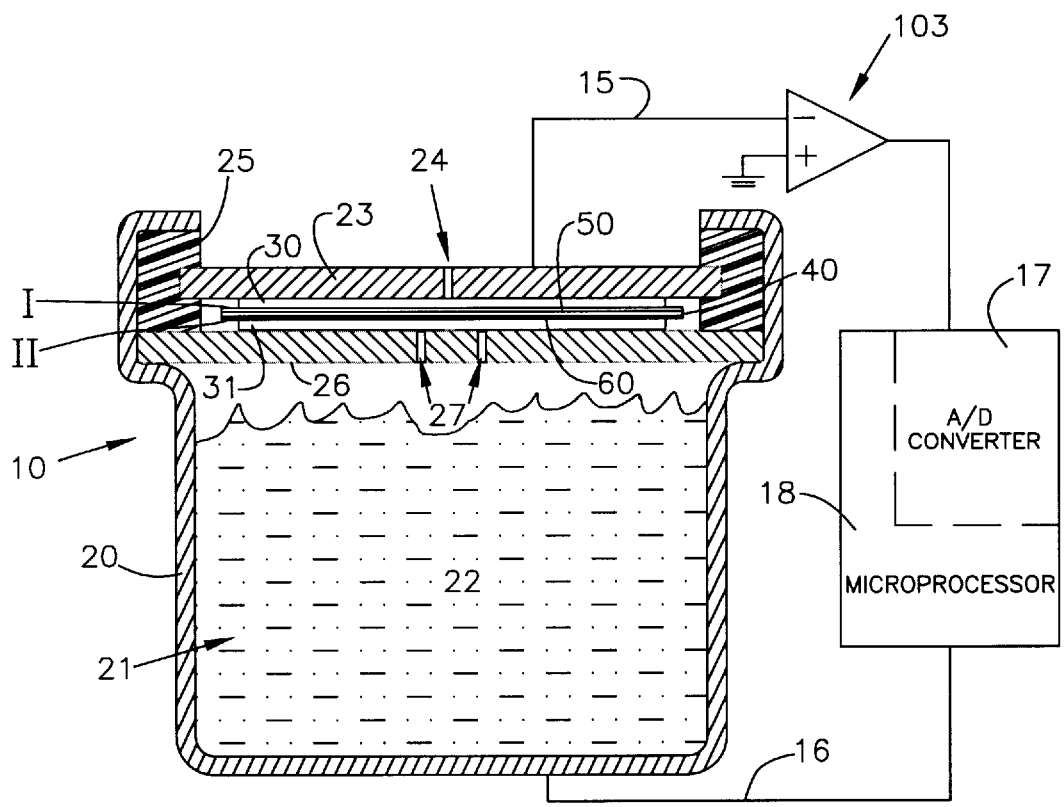
FIG. 2 is cross section view of a preferred embodiment of an electrochemical toxic gas sensor in accordance with the present invention, showing electrically conductive, hydrophobic top and bottom membranes positioned adjacent electrodes.

FIG. 2 shows a preferred embodiment of electrochemical toxic gas sensor 10 having an ion conducting solid electrolyte membrane 40 positioned between and in electrical contact with a first, sensing electrode 50 and a second, electrode 60. Introduction of CO to the first electrode produces an electrochemical reaction. More specifically, an oxidation reaction occurs at the first electrode, where CO is oxidized into carbon dioxide, and protons and electrons are generated by the reaction. The protons, which are of course ions of hydrogen, migrate across the solid electrolyte membrane 40 to the second electrode 60 where they react with electrons and oxygen to form water in a reduction reaction. This electrochemical reaction generates an electric signal which is proportional to the concentration of CO at the sensing electrode. Sensor 10 is electrically connected through lead 15, amplifier 103, and lead 16 to a measurement device, shown in FIG. 2 as a microprocessor 18 with an A/D converter 17 formed as part of the microprocessor. The microprocessor measures the digital signal from A/D converter 17 and generates an output signal corresponding to the sensed concentration level of CO. As mentioned above, the output signal can be directed to a display, and/or alarm, depending upon the concentration level to generate a display indicating the sensed concentration level of CO.

For the reaction to be continued, protons and electrons must be removed from the reaction sites, and CO and water vapor must be continuously provided to the reaction sites of the electrodes. Preferably each electrode comprises a mixed ionic-electronic conductive material. The electronic conducting materials pass electrons from the reaction sites while the protonic conducting materials pass protons from the reaction sites. This is important for continuing the electrochemical reaction and proper electrical signal generation.

The solid electrolyte 40 preferably comprises a membrane of a perfluorosulfonate ionomer such as those supplied by DUPONT under the trademark NAFION(TM) 117, PALL RAI's R4010 membrane or those supplied by DOW under the trademark XUS-1304. NAFION(TM) membranes incorporate PTFE like backbones with perfluorocarbon sulfonate sidechains to facilitate ion transport across the membrane. NAFION(TM) membranes have a preferred thickness in the range of approximately 0.05 to 1 mm, although NAFION (TM) membranes with smaller thicknesses could be used if they are commercially available. Generally it is preferable to minimize internal resistance of the sensor, and therefore it is desirable to make such protonic conductive electrolyte membranes thin, for example, 0.13 mm. The XUS membranes are similar to NAFION with PTFE like backbones but contain much shorter sidechains of the form [—O—$CF_2$—$CF_2$—$SO_3^-$]. Examples of other solid electrolytes can be found in PROTON CONDUCTORS, SOLID, MEMBRANES AND GELS—MATERIALS AND DEVICES, edited by Philippe Colomban, Cambridge University Press, 1992. Other suitable materials for use as an ion conducting solid electrolyte 40 will be readily apparent to those skilled in the art given the benefit of this disclosure.

Solid ion conducting electrolyte membranes such as NAFION(TM) typically have a content of water. 10% of the weight of the membrane 40 can be water in a saturated condition. The amount of water in the NAFION(TM) affects the rate of ion migration. If the membrane is exposed to ambient air, it will dry out, thereby changing the rate of ion migration which in turn changes the electric signal generated by the sensor 10. To avoid this, in preferred embodiments water reservoir 21 is provided in the housing 20 and contains at least a quantity of liquid water or other aqueous liquid. Slow evaporation of water 22 through vapor through holes 27 of bottom washer 26 will supply enough water vapor to keep the sensor 10 at constant hydration for many years, preferably at least ten years. Preferably the vapor through holes 27 are relatively small and relatively few, (just 2 are shown in FIG. 2) to help prevent leakage around the edge of the bottom membrane 31.

The ion conducting membrane 40 and first and second electrodes 50, 60, respectively, are preferably made as thin as possible to reduce internal ionic resistance. In one example, membrane 40 has a thickness of 0.13 mm and the electrodes 50, 60 each have a thickness of 0.006 mm. The electrodes 50, 60 may be deposited on membrane 40 so that the electrodes are formed as s single unit with membrane 40. Electrodes 50, 60 preferably can comprise, for example, a composite or a mixture of a platinum carbon mix forming an electronic conducting material and NAFION forming a proton conducting material. Preferably 10–50% by weight of each electrode comprises the ion conducting material, and 50–90% by weight of each electrode comprises the electronic conducting material.

The electrodes 50, 60 are sensitive to exposure to liquid water, in part because of the ions which exist in liquid water due to dissociation of water molecules. That is, in liquid water, a certain percentage exists as hydroxide ions and protons. The amount of protons present affects the rate of the electrochemical reaction, which can in turn affect the electric signal generated by the sensor. To protect the first electrode 50 from exposure to liquid water, an electrically conductive, hydrophobic top membrane 30 is positioned between the sensing hole 24 in the top washer 23 and the first electrode. The top membrane 30 serves many important functions in the sensor. By being hydrophobic, water from the external environment cannot pass through the sensing hole and reach the first electrode 50. By being electrically conductive and in direct contact with the first electrode 50, the top membrane 30 electrically connects the first electrode 50 with the measurement device, microprocessor 18. The top washer 23 is not in direct physical contact with the first electrode 50. In addition, the top membrane is microporous, permitting CO to diffuse through the membrane and increase the number of reaction sites along the first electrode.

Similarly, to protect the second electrode 60 from exposure to water from the water reservoir, an electrically conductive bottom membrane 31 is positioned in between the bottom washer 26 and the second electrode 60 so that the second electrode 60 is not in direct physical contact with the bottom washer 26. By being hydrophobic, water from the water reservoir 21 cannot pass through the vapor through holes 27 and reach the second electrode 60. By being electrically conductive and in direct contact with the second electrode 60, the bottom membrane 31 electrically connects the second electrode 60 with the measurement device, microprocessor 18. The bottom membrane is also microporous so as to be gas permeable, allowing water vapor from the reservoir 21 to pass through it to reach the electrodes 50, 60 and the solid electrolyte membrane 40, thereby producing constant relative humidity. As used here, the term hydrophobic is intended to mean that the membrane is impervious to liquid water. The membranes may also preferably be microporous, that is, sufficiently permeable to permit water vapor to pass from the reservoir 22 to the solid electrolyte membrane 40 in quantities sufficient for operation of the sensor in its intended fashion.

Examples of materials for the electrically conductive, hydrophobic top and bottom membranes 30, 31 include CARBEL TM carbon composites from W. L. Gore and Associates, or ELAT(TM) carbon composites from E-TEK. In one preferred embodiment where the CARBEL(TM) composites are used the top and bottom membranes 30, 31 each have a thickness of 0.24 mm. In one preferred embodiment where ELAT(TM) is used the top and bottom membranes each have a thickness of 0.20 mm. Other suitable electrically conductive hydrophobic membranes will be readily apparent to those skilled in the art given the benefit of this disclosure.

Although exposure to liquid water should be avoided, the electrodes and the electrolyte conducting membrane can be exposed to water vapor without disrupting the electric signal, and in fact need water vapor to function properly. The reason for this difference is that water is not dissociated in the gas phase as it is in the liquid phase. More specifically, electrostatic attraction between the proton and the hydroxide ion is quite strong. In order to separate the proton from the hydroxide ion, they must be surrounded (i.e., solvated) by lots of water molecules. That is not possible in the gas phase, unless the water molecules are subjected to very high energy. In other words, protons exist in the liquid phase of water, but do not exist in the vapor phase of water. The top and bottom membranes 30, 31 are advantageously also ion insulating, preventing dissociated protons from reaching the electrodes and the electrolyte membrane. The term ion insulating, as used here, is intended to mean that the membranes 30, 31 are impermeable to ions sufficient to protect the solid electrolyte membrane for operation of the sensor in its intended fashion.

It can be seen that the sensor forms a seven layer sandwich, with electrolyte membrane 40 having first and second electrodes 50, 60 positioned on opposite sides of the membrane 40. Positioned above the first electrode 50 is the top electrically conductive hydrophobic membrane 30 and positioned below the second electrode is the bottom electrically conductive hydrophobic membrane 31. Completing the sandwich, top washer 23 is positioned over top membrane 30, and bottom washer 26 is positioned below bottom membrane 31. Preferably this sensor componentry is assembled under pressure between the top washer and the bottom washer. This enhances electrical and ionic communication through the sensor, and it also prevents liquid water from leaking around the edges of the bottom membrane 31. Loading the sensor 10 under pressure helps to ensure that a stable electric signal is generated irrespective of position. An elastomeric seal 25 can be positioned between the top washer and the bottom washer 26, with a portion of housing 20 crimped around the top washer 30 to squeeze the top washer toward the bottom washer. The seal 25 is preferably a rubber free of chlorine or sulfur, or other elements which would poison the catalytic electrodes 50, 60.

Figure 3:
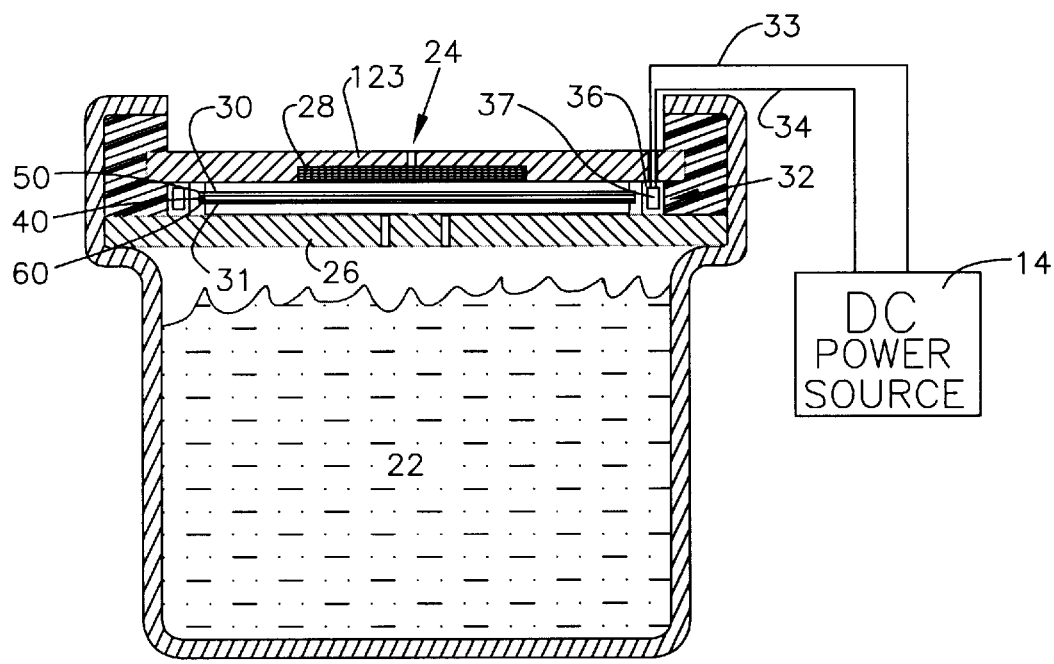
FIG. 3 is a cross section view of an alternative preferred embodiment of a toxic gas sensor in accordance with the present invention, showing a steel screen positioned between the top washer and the top electrically conductive, hydrophobic membrane, as well as a low temperature operation feature.

FIG. 3 shows an alternative preferred embodiment of a toxic gas sensor where grater diffusion of the gas to be sensed may be achieved, if desired, by enlarging an opening behind the sensing hole 24 and inserting a gas diffuser 28 which can be, for example, a stainless steel screen or mesh 28 positioned between the electrically conductive, hydrophobic membranes 30 and the top washer 123.

Figure 4:
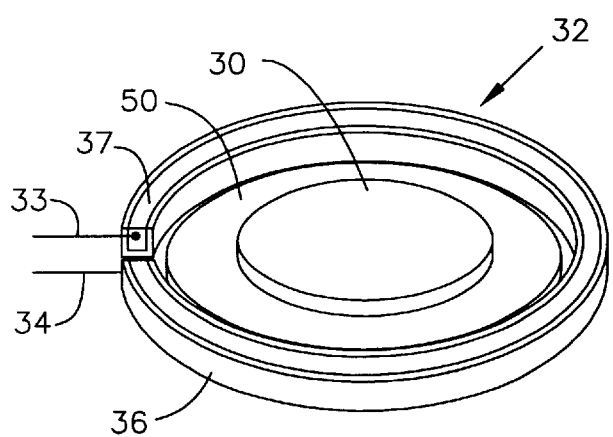
FIG. 4 is a perspective view, showing the heating element of the sensor of FIG. 3 forming a ring around the ion conducting electrolyte membrane.

As discussed above, water bonds to the solid electrolyte 40, and water vapor is required to maintain constant relative humidity and avoid disrupting the electric signal of the sensor. Temperatures much below the freezing point of the aqueous liquid can adversely affect sensor performance. FIGS. 3–4 show one preferred embodiment of a low temperature operation feature. Heating element 32 forms a ring around the solid electrolyte 40. The heating element 32 is connected to a dc power source 14. As electricity is passed through the heating element, heat is generated from resistance to the current, and this heat keeps the solid electrolyte membrane 40 warm, preferably in a temperature range between the freezing point and the boiling point of the liquid.

The heating element 32 comprises a resistance element 37 which conducts electricity and generates heat, and an insulating element 36 which electrically isolates the heating element from the electrolyte membrane 40 and the electrodes 50, 60. Optionally a thermistor 101 can be electrically connected to the microprocessor 18, so that the microprocessor directs the power source to pass current through the heating element 32 only when the temperature sensed by the thermistor falls below a certain level, such as the freezing point of the liquid. Other designs for heating elements positioned generally proximate to the electrolyte membrane will be readily apparent to those skilled in the art given the benefit of this disclosure.

Numerous self-diagnostic features can be used with the gas sensor of the present invention. The diagnostic feature provides a check to determine whether the sensor is functioning properly. If the sensor is malfunctioning, or has reached the end of its useful life as is the case when the water has completely evaporated from the water reservoir, then an output signal can be sent to an alarm to indicate this fact, so that the toxic gas detector can be replaced.

Figure 5:
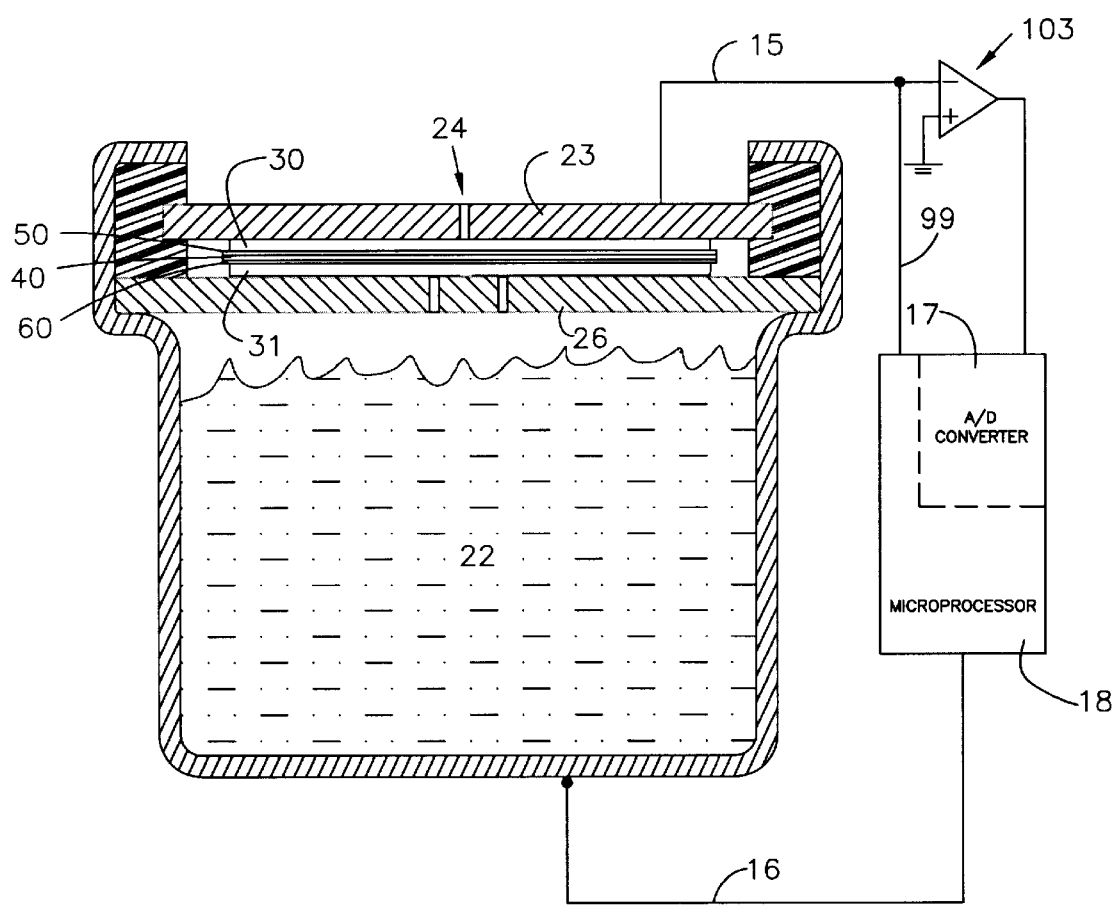
FIG. 5 is a cross section view of a preferred embodiment of an electrochemical toxic gas sensor in accordance with the present invention wherein the sensor has a self-diagnostic feature including a power source electrically connected across the sensor.
Figure 6:
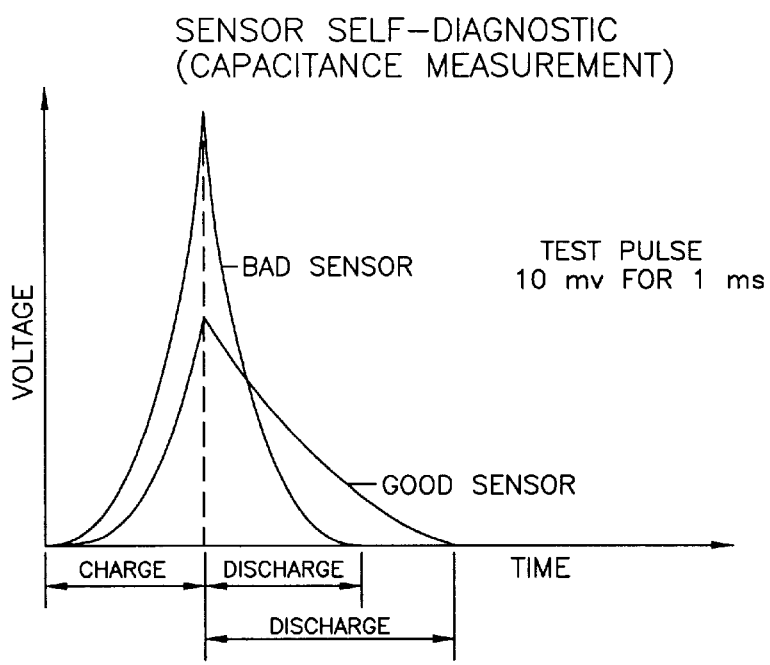
FIG. 6 is a graph of voltage vs. time for an electrochemical sensor incorporating a self-diagnostic feature of the present invention, where a DC pulse is applied briefly across; the electrodes where no electrochemical reaction takes place. For comparison, the output of a properly functioning sensor and a sensor that is not functioning properly is shown.
Figure 7:
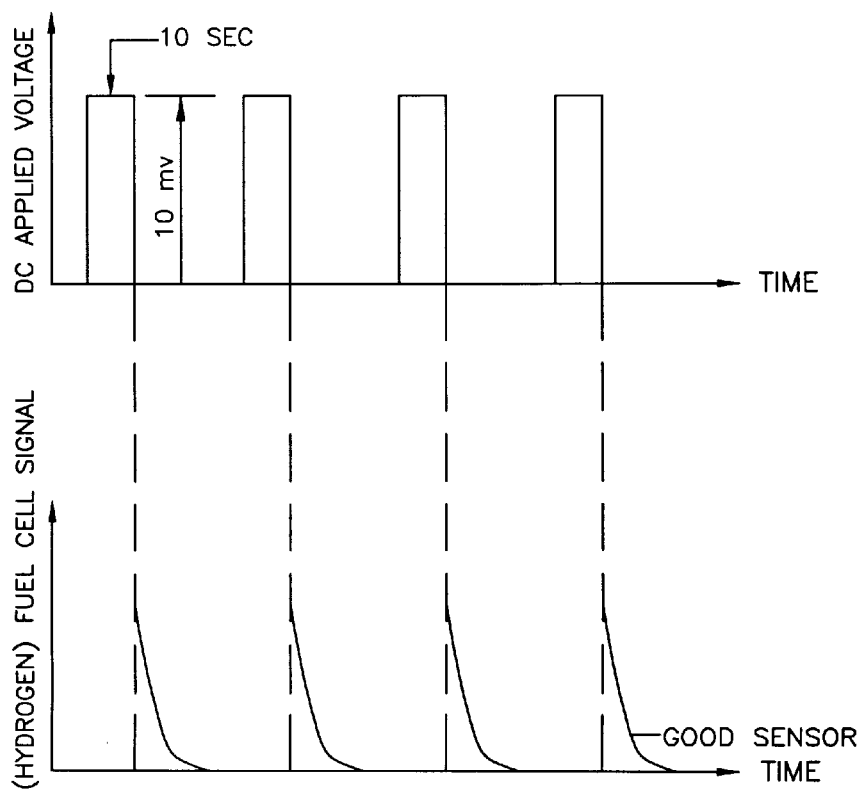
FIG. 7 is a graph of voltage vs. time for a sensor in accordance with FIG. 5 when a DC pulse is applied across the sensor for a period of time sufficient to generate an electrochemial reaction, showing the output voltage of a properly functioning sensor.
Figure 12:
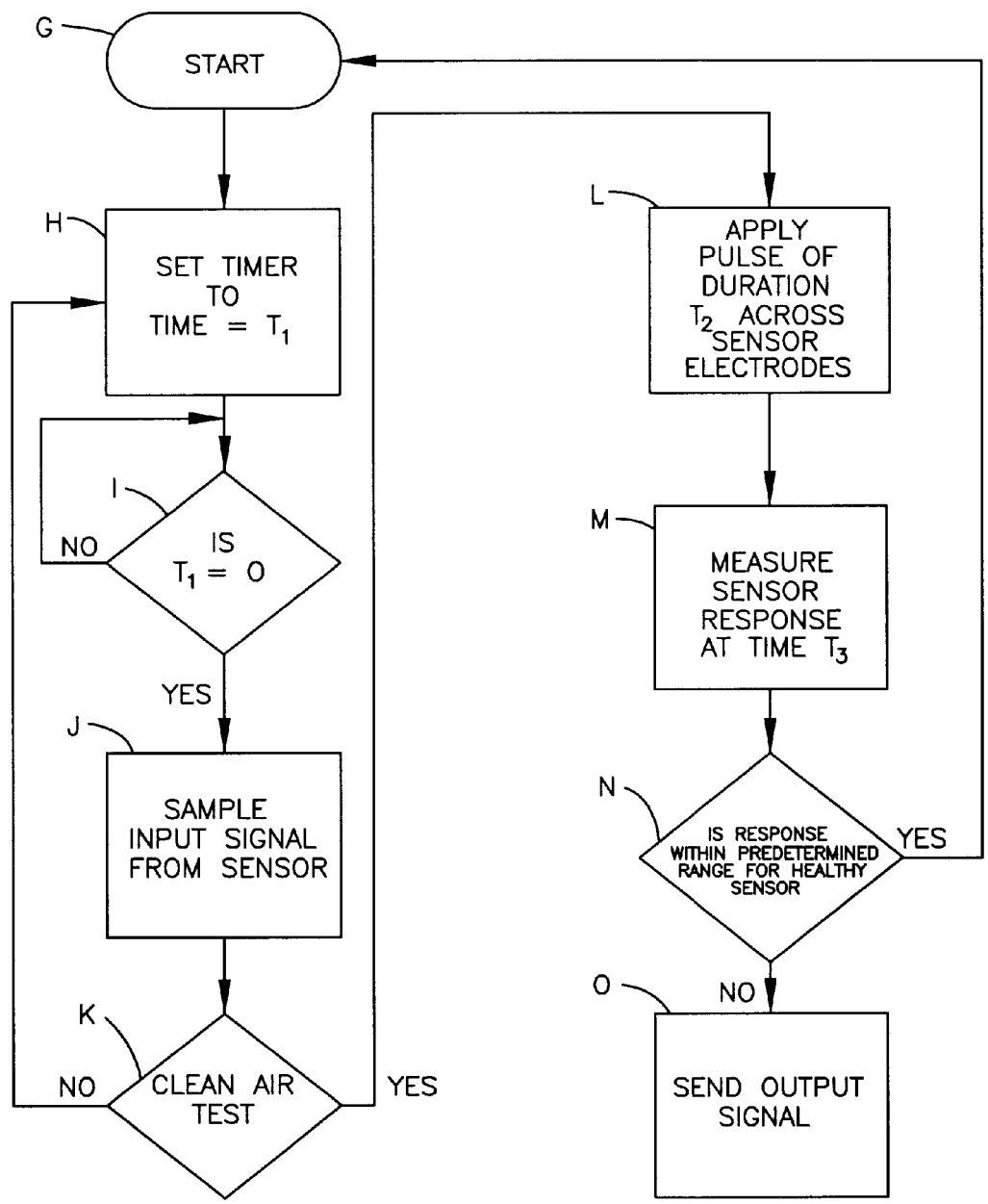
FIG. 12 shows a flow chart for a preferred operation of an internal self-diagnostic feature.

FIGS. 5, 6, 7, and 12 discuss two internal self-diagnostic techniques which can be used with a programmed processor. The first self-diagnostic feature can be referred to as capacitance measurement (FIGS. 5–6, and 12) and the second self-diagnostic feature can be referred to as fuel cell discharge measurement (FIGS. 5, 7, and 12).

When electric current flows into a capacitor, a force is established between two parallel plates separated by a dielectric. The energy is stored and remains even after the input is removed. By connecting a conductor (e.g., a hard wire) across the capacitor, the charged capacitor can regain electron balance, that is, discharge its stored energy. When carbon monoxide or other reactive gases are not present at the first electrode 50 the sensor 10 acts as a capacitor. In FIG. 5 the microprocessor 18 in the toxic gas detector 11 directs a small voltage to be applied across the sensor 10 through lead 99 for a short period of time, for example, 10 mV for 1 msec. Applying such a voltage across the sensor for such a short period of time is insignificant in the sense that it does not create a measurable electrochemical reaction. Instead, the sensor acts as a capacitor and charges up until the voltage is removed, then it discharges, that is, the voltage differential between the electrodes decreases. The microprocessor 18 measures the electric signal of the sensor, typically the voltage, at a given time after the pulse has been applied to the sensor. This voltage can then be compared with a predetermined value range for a healthy sensor. The predetermined value range can be based upon, for example, the voltage across the sensor at the given time after a pulse has been applied when the sensor is first assembled and known to be functioning properly. The given time may be based upon, for example, the time it takes for the voltage to decrease by 90% from the peak level seen at the end interval the voltage is applied across the sensor.

FIG. 6 shows a graph comparing good, healthy sensors with bad, malfunctioning sensors over an entire test period, including a charging period and a discharging period. If the sensor is functioning properly, the sensor charges and discharges slowly, and as the graph in FIG. 6 shows voltage vs. time immediately after the pulse will show relatively lower voltage and take longer to discharge than for a malfunctioning sensor. If the sensor is not functioning properly, the sensor charges up more rapidly, to a higher level and discharges more rapidly.

FIG. 12 shows one embodiment of a logic block diagram for internal self-diagnostic feature of the toxic gas sensor. The sensor performs intermittent self-diagnostic tests, and the air must be clean when the self-diagnostic test begins. So, from Start G, a countdown timer is set at H for a preset interval, which could range anywhere from, for example, a few seconds (or fractions of a second) to as infrequently as once per month. At decision block I the timer is read. Once it reaches zero, then a microprocessor samples the input signal from the sensor 10 at J. At decision block K, if the sensor reads clean air, which is essentially zero, (e.g., less than 1 ppm), then a diagnostic pulse is applied across the sensor at step L for duration t2. If the sensor does not read zero the process is repeated until the initial parameters match the conditions which existed when the predetermined value range was calculated. Time t2, is the length of time the pulse is applied across the sensor. Once the pulse ends, the microprocessor monitors the signal received from the sensor at M for time t3 and compares the signal with a predetermined value range for a sensor that is functioning normally at decision block N. A measurement can occur once at Time t3, or alternatively, it can be a series of measurements compared with a series of predetermined value range voltage measurements. If the monitored voltage is not in the range of the predetermined value range for a healthy, normally functioning sensor, the microprocessor can generate an error signal, and the error signal can be communicated to, for example, the LCD display 19 (seen in FIG. 1) or the alarm 38, (step O) or both, as desired. If the sensor is functioning normally, then the process merely repeats at regular intervals of time t1. It is known that since the aqueous reservoir gradually loses the aqueous liquid that the aqueous liquid reservoir will eventually dry out. When it does the capacitance of the sensor can change by a relatively large amount, for example, by at least a factor of 2. Thus, the range of acceptable values for the predetermined value range can be fairly wide, reflecting the anticipated error signal generated by the sensor.

The microprocessor may also preferably be connected to a manually operable test button 39 which would direct an electric input to the microprocessor. Thus, the microprocessor 18 can be programmed to automatically check at regular intervals to see whether the sensor is functioning adequately, or a manual test can be performed. The time and duration of the electric pulse applied across the sensor can be modified and controlled through the use of commercially available microprocessors well known in the art.

The diagnostic pulse applied at step L in FIG. 12 can be for a relatively small voltage and for a very short period of time as discussed above. As an alternative technique for determining whether the sensor is functioning properly, a diagnostic dc pulse from power source 14 may be applied across the sensor 10 of FIG. 5, only this time, the voltage is applied across the sensor for a sufficiently long period of time that an electrochemical reaction takes place, for example, 10 mV for as long as, for example, 10 seconds. (See FIG. 7) For a healthy sensor in the presence of water vapor, where the dc pulse is applied for a relatively long period of time the following reactions occur. At one of the electrodes, depending upon the polarity of the dc pulse, water molecules are converted as follows:

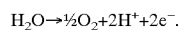

$H_2O \rightarrow \tfrac{1}{2}O_2 + 2H^+ + 2e^-$.

The protons migrate across the solid electrolyte membrane so that at the other electrode, hydrogen is formed:

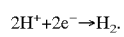

$2H^+ + 2e^- \rightarrow H_2$.

Depending on the direction of current flow from the dc pulse, the reduction reaction may occur at either first electrode 50 or second electrode 60. FIG. 7 shows a graph of a series of pulses applied across the sensor long enough and of sufficient magnitude to produce an electrochemical reaction. Once the dc pulse ends, the reaction will automatically reverse, the hydrogen will be consumed by the sensor and an electric signal will be generated, assuming the sensor is healthy. If the sensor is not healthy, hydrogen generation will be minimal or nonexistent, and no output will be detected from the sensor. As before, the microprocessor 18 can direct the magnitude and duration of the dc pulse, can compare the electric signal generated by the sensor after the pulse with known values for a healthy sensor, and generate an output signal which can be sent to a display or an alarm. The microprocessor may also be programmed to control the self-diagnostic feature so as to not apply a voltage across the sensor when the sensor is already sensing carbon monoxide. For example, if the sensor detects anything more than a very small amount of a toxic gas such as one part per million, the programmed processor could prevent engagement of the self-diagnostic device. For both the capacitance and fuel cell self-diagnostic tests, a single self-diagnostic test may be sufficient, or multiple tests may be run and their results averaged or normalized.

Figure 8:
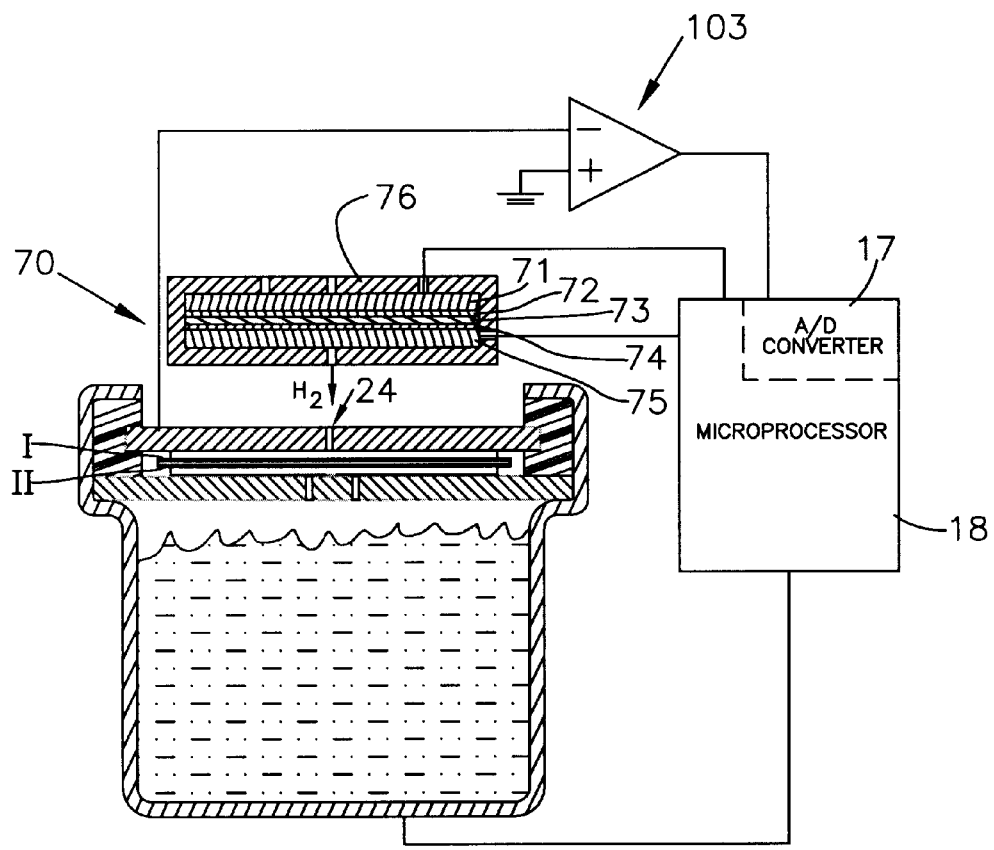
FIG. 8 shows an alternative preferred embodiment of a toxic gas sensor in accordance with the present invention having a diagnostic feature which is mounted external of the sensor comprising a hydrogen gas generating device.
Figure 9:
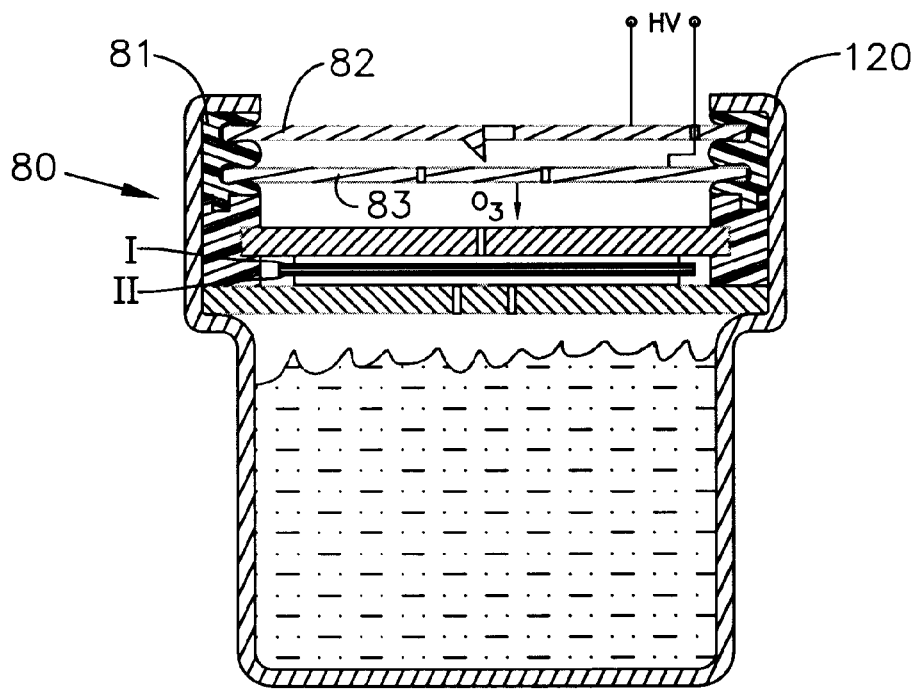
FIG. 9 shows an alternative preferred embodiment of a toxic gas sensor in accordance with the present invention having a diagnostic feature which is mounted external of the sensor comprising an ozone generating device.
Figure 10:
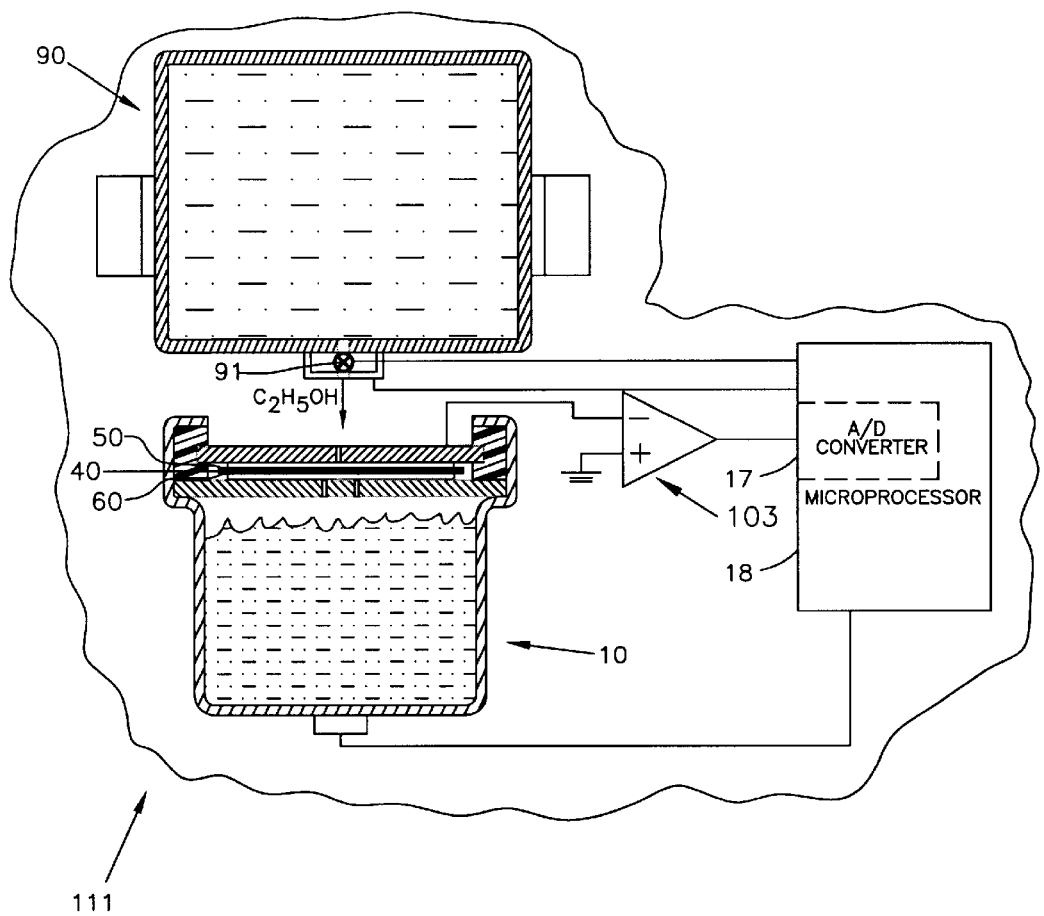
FIG. 10 shows an alternative preferred embodiment of a toxic gas sensor in accordance with the present invention having a self-diagnostic and/or self-calibration feature mounted external of the sensor comprising a liquid reservoir with a microprocessor controlled microvalve for intermittent, measured release of a reactive chemical to which the sensor is sensitive.

Such internal self-diagnostics are good for basic testing of the health and functionality of the sensor. It may also be desirable to provide a sensor having a self-diagnostic feature which can sense whether the sensing hole is plugged. FIGS. 8–10 disclose three alternative preferred embodiments of a toxic gas sensor having self-diagnostic features mounted externally of the sensor, where a reactive chemical is introduced to the sensor at the sampling hole 24. By reactive chemical, it is meant a chemical which reacts in the sensor at the first electrode to generate an electric signal.

Figure 13:
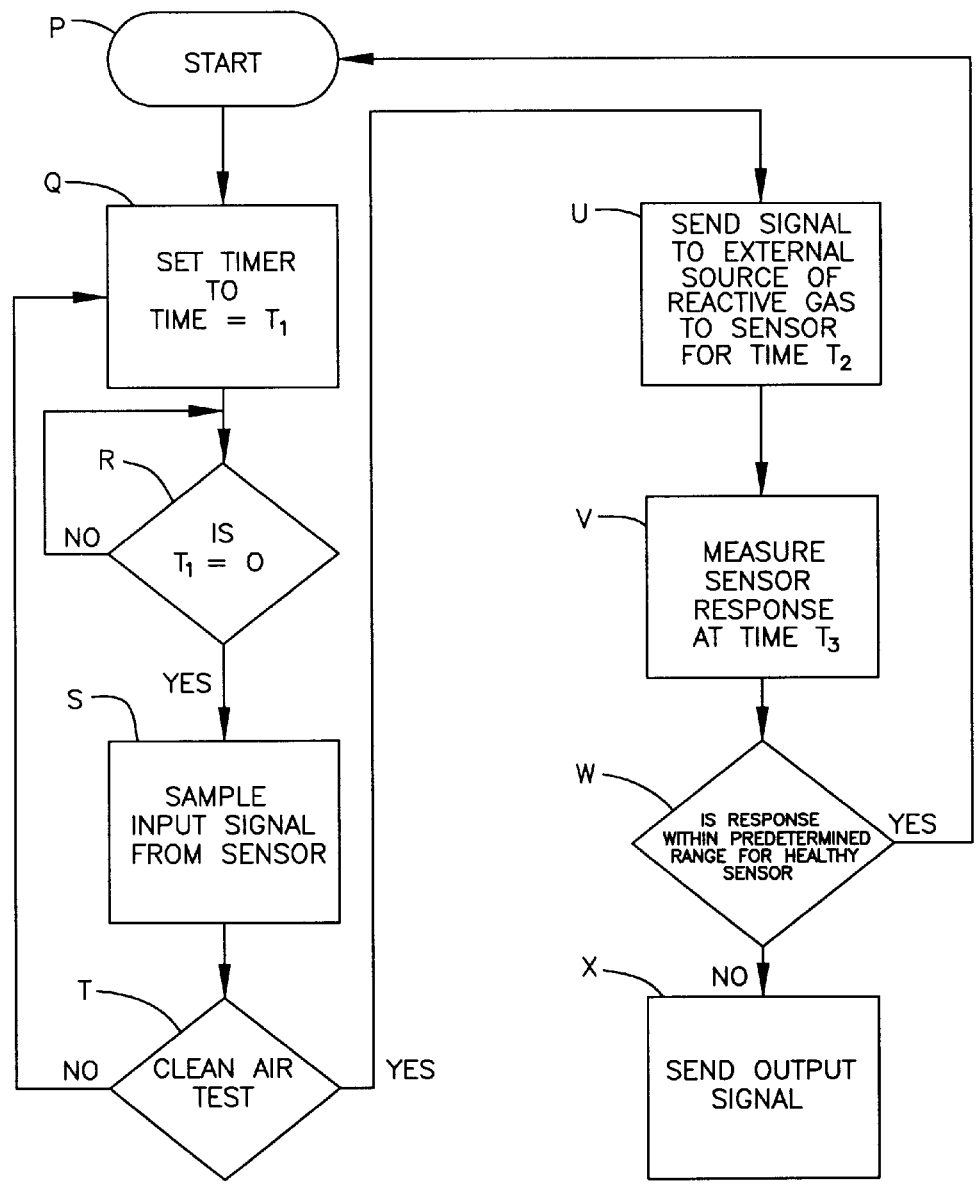
FIG. 13 shows a flow chart for a preferred operation of an external self-diagnostic feature.

FIG. 13 shows one preferred embodiment of a logic block diagram for an externally mounted self-diagnostic feature. Steps P–T are similar to steps G–K in for the internal self-diagnostic features discussed in FIG. 12, and serve to set the interval of time between self diagnostic tests and ensure that the sensor is sensing clean air, i.e, not currently sensing a toxic gas. At step U an output signal is directed to the external source, releasing the reactive gas, (which could include generating a reactive gas) typically in the vicinity of the sampling hole. The interval of the signal is time t2. At step V the microprocessor measures the sensor response at a time interval t3, and at decision block W the microprocessor compares the electric signal received from the sensor with a known or predetermined value range for a healthy sensor. Time t3 can encompass a single measurement and be compared with a single predetermined voltage value range, or alternatively, a series of measurements can be made over time interval t3 and compared with a series of predetermined value ranges at each interval over time t3. As above, the predetermined value range can be based upon measurements of the sensor taken when the sensor is first assembled and known to be healthy. An output error signal can be sent to an alarm at step X or to a display, or both if the sensor is faulty and/or has reached the end of its useful life. If the sensor signal response is within the predetermined range for normally functioning sensors then the process can be repeated at regular intervals. As indicated above, the electric signal may be conditioned before reaching the microprocessor, as for example by passing the electric signal through a low input impedance amplifier and an A/D converter. In this way the microprocessor is comparing a digital value with a known digital value range for a healthy sensor.

In FIG. 8, the reactive chemical is hydrogen, and an external generator 70 of hydrogen is provided in close proximity to the sensing hole 24. A dc pulse is passed through the hydrogen generator 70. The hydrogen generator 70 works in a manner similar to the sensor in that it has a housing 76, a top electrically conductive, gas permeable hydrophobic membrane 71, a first, sensing electrode 72, a proton conducting electrolyte membrane 73, a second, electrode 74 and a bottom, electrically conductive gas permeable membrane 75. In response to the dc pulse, water vapor which passes through openings in the housing 76 and diffuses through the top membrane 71 to reach the first electrode 72, where the water is catalyzed into oxygen, protons and electrons. The protons migrate across the protonic conductive membrane 73 to the second electrode 74 where they react with electrons to form hydrogen. The hydrogen gas diffuses through the bottom membrane 75 and out to the sampling hole 24 of the toxic gas sensor 10. If the sampling hole is unplugged and the sensor is functioning normally, the sensor will consume the hydrogen in the reactions shown in FIG. 8, reversing the reaction that initially generated the hydrogen, producing water vapor and an electric signal. Advantageously, the self-diagnostic test can be performed intermittently as a routine check on the health of the sensor. The electric signal can be measured by microprocessor 18, compared by a comparator (which can be part of the microprocessor) with known values for a healthy sensor, and an output signal can be generated to indicate the health of the sensor.

FIG. 9 shows an alternative preferred embodiment of a toxic gas sensor provided with an external self-diagnostic feature where the reactive chemical is ozone. An ozone generator 80 is positioned in close proximity to the sensor's sampling hole, and can be incorporated within the sensor's housing 120. Two electrically conductive plates 82, 83 are positioned adjacent one another, separated by an insulating spacer. A large potential difference (for example, several hundred volts) is generated between the plates. This high voltage causes a spark to jump between the plates. Oxygen in the air, in the presence of electricity forms ozone, $O_3$. The ozone migrates to the sensing hole of the sensor. If the sampling hole is unplugged and the sensor is functioning normally, the sensor will consume the ozone in the reactions shown in FIG. 9, reversing the reaction that initially generated the ozone, producing oxygen, water vapor and an electric signal.

The electric signal can be measured by a microprocessor, compared with known values for a healthy sensor, and an output signal can be generated to indicate the health of the sensor.

FIG. 10 shows another alternative preferred embodiment of a toxic gas sensor having an externally mounted self-diagnostic feature where the reactive gas is ethanol ($C_2H_5OH$), an alcohol. A small tank 90 of ethanol is mounted on the toxic gas detector 111 in close proximity to the sensor. In response to a control signal from microprocessor 18, a microvalve 91 opens, releasing an measured amount of ethanol from the tank. The ethanol reacts at the first electrode 50 to form protons and electrons and generate an electric signal. In a manner similar to the other self-diagnostic embodiments discussed above, the electric signal can be measured by the microprocessor and an output signal can be generated which can be sent to a display or a buzzer, or both. Preferably enough ethanol is held in the tank 90 so that self-diagnostic testing can be conducted beyond the anticipated useful life of the sensor. Other alcohols and suitable reactive chemicals useful in self-diagnostic systems will be readily apparent to those skilled in the art given the benefit of this disclosure.

Releasing a measured amount of a reactive chemical will generate given measurable electric signal in a healthy sensor at a given time. This given electric signal can be stored as a known value in the microprocessor. Advantageously, this allows the self-diagnostic element to act as a calibration feature as well. The microprocessor directs a measured amount of a reactive chemical to be released. This generates an electric signal which can be compared by a comparator with the known value range for a healthy sensor. If the electric signal from the sensor is not the same as the known value, the microprocessor can adjust its output signal to compensate for the difference. This can be done, for example, by applying a bias voltage or by resetting the initial parameters for a new zero reading.

From the foregoing disclosure and detailed description of certain preferred embodiments, it will be apparent that various modifications, additions and other alternative embodiments are possible without departing from the true scope and spirit of the invention. For example, gas sensors of this type can find ready application in automobiles, recreational vehicles, and scientific instruments where it is important to monitor levels of carbon monoxide or other toxic gases. Advantageously, toxic gas sensors as discussed here can have tolerances of just a few parts per million of toxic gas. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A gas sensor comprising, in combination:
   a first electrode and a second electrode;
   an ion conducting, solid electrolyte membrane positioned between the first electrode and the second electrode, wherein ions migrate through the solid electrolyte membrane in response to the presence of a reactive gas at the first electrode; and
   a diagnostic device for diagnosing whether the sensor is operating properly, comprising:
   A) an applied voltage source coupled to the first electrode and the second electrode;
   B) a programmed processor, coupled to at least one of the electrodes and to the applied voltage source for
      i. applying a predetermined applied voltage across the electrodes during at least one charging portion of at least one test period
      ii. monitoring a monitored voltage across the electrodes in a discharge portion which occurs after the at least one charging portion of the test period and;
      iii. generating an output error signal if the monitored voltage corresponds to a faulty condition.

2. The gas sensor of claim 1 wherein the applied voltage is of sufficiently low magnitude and duration that no significant amount of ions migrate through the solid electrolyte membrane, and the monitored voltage is a voltage differential between the first electrode and the second electrode, and the programmed processor monitors the rate of decrease of the monitored voltage.

3. The gas sensor of claim 1 wherein the applied voltage is of sufficient magnitude and duration that in a gas sensor which is operating properly a reactive chemical is generated at one of the electrodes while the power source is applied, and after the power source is removed the volatile chemical is oxidized at the one of the electrodes, generating the electric signal.

4. The gas sensor of claim 1 wherein the programmed processor prevents actuation of the diagnostic device between the first electrode and the second electrode when the gas is present at the first electrode when the reactive gas is present at the first electrode.

5. The gas sensor of claim 1 wherein the programmed processor comprises an analog to digital converter for receiving the electric signal, coupled to at least one electrode for converting an analog voltage value to a corresponding digital voltage value.

6. The gas sensor of claim 1 wherein the programmed processor compares the monitored voltage with a predetermined value range for a sensor which is functioning properly and produces the output error signal.

7. The gas sensor of claim 6 further comprising an alarm electrically connected to the output error signal for indicating that the sensor is not functioning properly.

8. A gas sensor comprising, in combination:
   a first electrode and a second electrode;
   an ion conducting, solid electrolyte membrane positioned between the first electrode and the second electrode, wherein ions migrate across the solid electrolyte membrane in response to the presence of a first gas sensed at the first electrode; and
   a diagnostic device for diagnosing whether the sensor is operating properly, comprising:
   A) an external source of a second, reactive gas different from the fist gas which when introduced to the first electrode generates an electric signal between the first electrode and the second electrode;
   B) a programmed processor, coupled to at least one of the electrodes and the external source of the second, reactive gas
      i. sending a control signal to the external source at a predetermined interval to release the second, reactive gas to the first electrode, and
      ii. monitoring a monitored voltage across the electrodes after the release of the second, reactive gas to the first electrode.

9. The gas sensor of claim 8 wherein the second, reactive gas is an alcohol.

10. The gas sensor of claim 8 wherein the second, reactive gas is hydrogen.

11. The gas sensor of claim 8 wherein the second, reactive gas is ozone.

12. The gas sensor of claim 8 wherein the external source has a release valve which opens and closes in response to a control signal from the programmed processor, permitting intermittent release of the second, reactive gas to the first electrode.

13. The gas sensor of claim 8 wherein the programmed processor comprises an analog to digital converter for receiving the electric signal, coupled to at least one electrode for converting an analog voltage value to a corresponding digital voltage value.

14. A gas sensor comprising, in combination:
    a first electrode and a second electrode;
    an ion conducting, solid electrolyte membrane positioned between the first electrode and the second electrode, wherein ions migrate across the solid electrolyte membrane in response to the presence of a first gas sensed at the first electrode; and
    calibration means for calibrating the sensor, comprising
    A) an external source of a reactive gas which when introduced to the first electrode generates an electric signal between the first electrode and the second electrode,
    B) a programmed processor, coupled to at least one of the elects and external source of the reactive gas i. sending a control signal to the external source at a predetermined interval to release a controlled amount of the reactive gas to the first electrode,
ii. monitoring a monitored voltage across the elect after the release of the reactive gas to the first electrode, and
iii. comparing the monitored voltage with a predetermined value range for a sensor which is functioning properly and produces an output which compensates for any difference between the electric signal and a known electric signal;

wherein the programmed processor prevents release of the reactive gas to the first electrode when a measurable amount of the first gas is present at the first electrode.

* * * * *